(12) United States Patent
Somberg et al.

(10) Patent No.: US 11,286,235 B2
(45) Date of Patent: *Mar. 29, 2022

(54) ULTRA SHORT ACTING ANTI-ARRHYTHMIC AGENTS

(71) Applicant: Academic Pharmaceuticals Incorporated, Lake Bluff, IL (US)

(72) Inventors: John Somberg, Lake Forest, IL (US); Robert J Chorvat, Chadds Ford, PA (US)

(73) Assignee: Academic Pharmaceuticals, Incorporated, Lake Bluff, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/063,497

(22) Filed: Oct. 5, 2020

(65) Prior Publication Data

US 2021/0107867 A1  Apr. 15, 2021

Related U.S. Application Data

(63) Continuation of application No. 16/398,368, filed on Apr. 30, 2019, now Pat. No. 10,793,519.

(60) Provisional application No. 62/665,584, filed on May 2, 2018.

(51) Int. Cl.
 C07C 311/08 (2006.01)
 C07C 311/24 (2006.01)
 A61P 9/06 (2006.01)
 C07C 311/00 (2006.01)

(52) U.S. Cl.
 CPC .............. *C07C 311/08* (2013.01); *A61P 9/06* (2018.01); *C07C 311/00* (2013.01); *C07C 311/24* (2013.01)

(58) Field of Classification Search
 CPC ........................... C07C 311/08; C07C 311/24
 See application file for complete search history.

(56) References Cited

U.S. PATENT DOCUMENTS

| | | | |
|---|---|---|---|
| 3,341,584 A | 9/1967 | Larsen et al. | |
| 4,404,224 A | 9/1983 | Asato | |
| 6,750,238 B1 | 6/2004 | Erhardt | |
| 6,756,047 B2 | 6/2004 | Erhardt et al. | |
| 7,049,326 B2 | 5/2006 | Erhardt | |
| 7,164,027 B2 | 1/2007 | Erhardt | |
| 10,793,519 B2 * | 10/2020 | Somberg | ............... C07C 311/24 |

* cited by examiner

*Primary Examiner* — Matthew P Coughlin
(74) *Attorney, Agent, or Firm* — Vance Intellectual Property, PC (57) ABSTRACT

The present invention provides novel sotalol derivatives and pharmaceutical compositions containing the same that are are useful as pharmaceutical agents in the treatment of supraventricular and ventricular arrhythmias.

16 Claims, 2 Drawing Sheets

ULTRA SHORT ACTING ANTI-ARRHYTHMIC AGENTS

FIELD OF THE INVENTION

The present invention relates to novel sotalol derivatives and pharmaceutical compositions containing the same. The derivatives and compositions are useful as pharmaceutical agents in the treatment of supraventricular and ventricular arrhythmias.

BACKGROUND OF THE INVENTION

There is a clinical need for a short acting effective anti-arrhythmic agent for the treatment of both supraventricular and ventricular arrhythmias in patients with arrhythmias. Two effective agents are amiodarone and sotalol. Amiodarone has a very long half-life and a multitude of adverse toxicities. Sotalol is also an effective anti-arrhythmic, but its use is limited by the worsening of arrhythmias at times, a problem termed proarrhythmia. While the half-life of sotalol in man is shorter than amiodarone, the half-life of sotalol is twelve hours on average, making the cessation of therapy if arrhythmias worsen, problematic. To dissipate, sotalol takes a long time, which can be a major clinical problem. The introduction of a short acting sotalol like drug would offer considerable advantage for the acute treatment of arrhythmias.

Therefore, it is desirable to discover sotalol-like compounds that metabolize faster than sotalol.

SUMMARY OF THE INVENTION

Accordingly, in an aspect, the present invention provides novel sotalol derivatives stereoisomers or pharmaceutically acceptable salts thereof.

In another aspect, the present invention provides novel pharmaceutical compositions, comprising: a pharmaceutically acceptable carrier and a therapeutically effective amount of at least one of the compounds of the present invention or a stereoisomer or pharmaceutically acceptable salt thereof.

In another aspect, the present invention provides novel methods of treating various therapeutic indications of sotalol by administering to a subject a therapeutically effective amount of a compound of the present invention.

In another aspect, the present invention provides compounds for use in medical therapy.

In another aspect, the present invention provides the use of compounds of the present invention for the manufacture of a medicament for the treatment of supraventricular and ventricular arrhythmias.

These and other objects, which will become apparent during the following detailed description, have been achieved by the inventors' discovery that the presently claimed compounds or stereoisomers or pharmaceutically acceptable salt forms thereof are expected to be effective as sotalol derivatives.

DETAILED DESCRIPTION OF THE INVENTION

All references cited herein are hereby incorporated in their entirety herein by reference.

A short acting sotalol derivative administered intravenously could be administered to patients in a supraventricular arrhythmia to affect termination. If the treating physician saw evidence of excessive QT prolongation, the IV sotalol derivative could be stopped, avoiding adverse effects that could entail life threatening ventricular arrhythmias such as ventricular tachycardia or ventricular fibrillation.

In the pediatric population, the use of IV sotalol has advantages over amiodarone, another anti-arrhythmic drug. Amiodarone has many adverse side effects (2) and its toxicity is especially problematic in pediatric patients (12, 13). In addition, sotalol is especially effective in some supraventricular arrhythmias that are unique to the pediatric patient. An arrhythmia post-operative, ectopic junctional tachycardia (JET) is especially susceptible to effective treatment employing sotalol (14). Utilizing a short acting sotalol derivative would terminate the arrhythmia and if toxicity develops from sotalol derivative, the drug action could be rapidly stopped, providing an extra safety margin in the pediatric patient.

A rapidly metabolized sotalol derivative could be used to slow atrial tachycardia, convert atrial tachycardia, slow the ventricular response to atrial fibrillation, convert atrial fibrillation, or atrial flutter. A rapid acting, short half-life drug would be especially effective in the post-operative coronary artery surgery patients. Oral sotalol has been shown effective in preventing the high incidence of AF post-operative (15). An IV short acting agent would be useful in this situation affording pharmacologic benefit, while if excessive, QT prolongation is noted, or ventricular arrhythmias develop, the agent could be stopped with rapid dissipation of the adverse pharmacologic actions. This agent would possess the efficacy advantages of sotalol with a new safety margin, offering considerable therapeutic advantage.

As a result, in an aspect, the present invention provides a novel sotalol derivative that is metabolized by human esterases faster than sotalol (~10-20 hours for terminal elimination half-life of sotalol). This novel beta-blocker/antiarrhythmic agent is expected to be rapidly metabolized so as to minimize the time of the desired activity of the administered agent and minimize the side effects due to prolonged exposure, which have been observed with sotalol.

In another aspect, the present invention provides a novel compound selected from Formulae 1-5:

| Formula # | Structure |
|---|---|
| 1 |  |

| Formula # | Structure |
|---|---|
| 2 |  |
| 3 |  |
| 4 |  |
| 5 |  | or a pharmaceutically acceptable salt thereof.

In another aspect, the present invention provides novel compounds of Formula 1 or a stereoisomer or a pharmaceutically acceptable salt thereof:

Formula 1 wherein:
R is selected from H, $C_{1-6}$ alkyl, $C_{3-6}$ alkenyl, and $C_{3-6}$ alkynyl;
m is selected from 0, 1, and 2;
X, $X^1$, $X^2$, and $X^3$ are independently selected from H, —O—$C_{1-3}$ alkyl, $C_{1-3}$ alkyl, halogen, $CF_3$, nitro, and —CN; and,
Y is selected from H and $C_{1-3}$ alkyl.

In another aspect, the present invention provides a novel compound of Formula 2 or a stereoisomer or a pharmaceutically acceptable salt thereof:

Formula 2 wherein:
R is selected from H, $C_{1-6}$ alkyl, $C_{3-6}$ alkenyl, and $C_{3-6}$ alkynyl;
m is selected from 0, 1, and 2;
X, $X^1$, $X^2$, and $X^3$ are independently selected from H, —O—$C_{1-3}$ alkyl, $C_{1-3}$ alkyl, halogen, $CF_3$, nitro, and —CN;
Y is selected from H and $C_{1-3}$ alkyl; and,
Z is from H, $CH_3$, $CH_2OH$, and $CH(CH_3)OH$.

In another aspect, the present invention provides a novel compound of Formula 3 or a stereoisomer or a pharmaceutically acceptable salt thereof:

Formula 3 wherein:
R is selected from H, $C_{1-6}$ alkyl, $C_{3-6}$ alkenyl, and $C_{3-6}$ alkynyl;
m is selected from 0, 1, and 2;
n is selected from 0, 1, 2, and 3; and,
X, $X^1$, $X^2$, and $X^3$ are independently selected from H, —O—$C_{1-3}$ alkyl, $C_{1-3}$ alkyl, halogen, $CF_3$, nitro, —CN.

In another aspect, the present invention provides a novel compound of Formula 4 or a stereoisomer or a pharmaceutically acceptable salt thereof:

Formula 4 wherein:
R is selected from H, $C_{1-6}$ alkyl, $C_{3-6}$ alkenyl, and $C_{3-6}$ alkynyl;
m is selected from 0, 1, and 2;
X, $X^1$, $X^2$, and $X^3$ are independently selected from H, —O—$C_{1-3}$ alkyl, $C_{1-3}$ alkyl, halogen, $CF_3$, nitro, —CN; and,
Y is independently selected from H, $C_{1-3}$ alkyl.

In another aspect, the present invention provides a novel compound of Formula 5 or a stereoisomer or a pharmaceutically acceptable salt thereof:

Formula 5 wherein:
R is selected from H, $C_{1-6}$ alkyl, $C_{3-6}$ alkenyl, and $C_{3-6}$ alkynyl;
n is selected from 0, 1, 2, and 3;
X, $X^1$, $X^2$, and $X^3$ are independently selected from H, —O—$C_{1-3}$ alkyl, $C_{1-3}$ alkyl, halogen, $CF_3$, nitro, and —CN; and,
Y is independently selected from H and $C_{1-3}$ alkyl.

In another aspect, the present invention provides a novel compound of Formula 1-5, or a stereoisomer or pharmaceutically acceptable salt thereof, wherein: one or more hydrogens (H) are replaced by D. For example, R can be a D, a deuterated methyl group (e.g., $CD_3$) or the alkenyl or alkynyl hydrogens can be replaced by deuterium (e.g., —CD=CD—). In addition, wherever hydrogens are present in one of the Formulae or in one of the listed substituents (R, X, Y, etc.), the hydrogens present (e.g., —$CH_2$—, alkyl, alkenyl, alkynyl, phenyl, etc.) can be partially or fully replaced by D (e.g., —$CD_2$—, $CD_3$, $d_1$-phenyl, etc.).

In another aspect, the present invention provides a novel pharmaceutical composition, comprising: a therapeutically effective amount of a compound of the present invention or a stereoisomer or a pharmaceutically acceptable salt thereof and a pharmaceutically acceptable carrier.

In another aspect, the present invention provides a novel compound having a terminal elimination half-life less than 10 hours. Additional examples include less than 9, 8, 7, 6, 5, 4, 3, 3, 2, and 1 hour. Further examples include less than 60, 50, 40, 30, 20, and 10 minutes. Terminal elimination half-life is the time it takes for 50% of the compound to be excreted or metabolized.

With the compounds of the present invention being short acting, they offer the advantage of a superior therapeutic to toxic ratio. In another aspect, the pharmacologic action of the compounds of the present invention can be quickly terminated by stopping administration thereof to avoid adverse side effects. In another aspect, the compounds of the present invention can prolong cardiac repolarization and then prevent the recurrence of the arrhythmia as long as adequate drug concentration is maintained.

In another aspect, the present invention provides a novel method of terminating or blocking the occurrence of an arrhythmia, comprising: administering to a patient in need thereof a therapeutically effective amount of a compound of the present invention or a stereoisomer or pharmaceutically acceptable salt thereof, wherein the arrhythmia is selected from: paroxysmal atrial tachycardia, junctional ectopic tachycardia, atrial flutter, atrial fibrillation, atrial tachycardia, junctional tachycardia, ventricular tachycardia, and ventricular fibrillation.

Blocking refers to preventing the recurrence of or reducting the frequency of recurrence of the indication for as long as the compound of the present invention is present in the patient at an effective concentration.

In another aspect, the present invention provides a novel method of causing electrophysiological actions that are anti-arrhythmic, comprising: administering to a patient in need thereof a therapeutically effective amount of a compound of the present invention or a stereoisomer or pharmaceutically acceptable salt thereof, wherein the compound binds to the IKr and possibly IKs potassium channels, inhibiting then.

In another aspect, the present invention provides a novel method of terminating a symptom selected from: paroxysmal atrial tachycardia, junctional ectopic tachycardia, atrial flutter, atrial fibrillation, atrial tachycardia, junctional tachycardia, ventricular tachycardia, and ventricular fibrillation, comprising: administering to a patient in need thereof a therapeutically effective amount of a compound of the present invention or a stereoisomer or pharmaceutically acceptable salt thereof.

In another aspect, the present invention provides a novel method of blocking the development of or blocking a symptom selected from: atrial tachycardia, junctional ectopic tachycardia, atrial flutter, atrial fibrillation, junctional tachycardia, ventricular tachycardia and ventricular fibrillation, comprising: administering to a patient in need thereof a therapeutically effective amount of a compound of the present invention or a stereoisomer or pharmaceutically acceptable salt thereof.

In another aspect, the patient had previously suffered from at least one of the symptoms and the therapy stops the reoccurrence of the symptom.

In another aspect, the present invention provides a novel method of treating a symptom selected from: paroxysmal atrial tachycardia junctional ectopic tachycardia, atrial flutter, and atrial fibrillation that occurs peri or post-operatively in the pediatric or adult population, comprising: administering to a patient in need thereof a therapeutically effective amount of a compound of the present invention or a stereoisomer or pharmaceutically acceptable salt thereof.

In another aspect, route of administration is selected from: intravenous, oral, topical, sublingual, and bucal.

In another aspect, the present invention provides a novel compound for use in therapy.

In another aspect, the present invention provides the use of novel compounds for the manufacture of a medicament for the treatment of an indication recited herein.

In another aspect, examples of the molecular weight of the compounds of the present invention include (a) less than about 500, 550, 600, 650, 700, 750, 800, 850, 900, 950, or 1000 grams per mole; (b) less than about 950 grams per mole; (c) less than about 850 grams per mole; and, (d) less than about 750 grams per mole.

In another aspect, examples of the solubility of the compounds of the present invention include greater than 50 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900 and 1000 µg/mL.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

A compound or compounds of the present invention, as used herein, includes, where appropriate, stereoisomers and/or pharmaceutically acceptable salts thereof.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

"Stable" means that the compound is suitable for pharmaceutical use.

The present invention covers stable compounds and thus avoids, unless otherwise specified, the following bond types: heteroatom-halogen, N—S, O—S, O—O, and S—S.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

When an "ene" terminates a group it indicates the group is attached to two other groups. For example, methylene refers to a —CH$_2$-moiety.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Cyclic amine" is a hydrocarbon ring wherein one carbon atom of the ring has been replaced by a nitrogen atom. The cyclic amine can be unsaturated, partially saturated, or fully saturated. The cyclic amine can also be bicyclic, tricyclic, and polycyclic. Examples of cyclic amine include pyrrolidine and piperdine.

"Halo" or "halogen" refers to fluoro, chloro, bromo, and iodo.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting its development; and/or (c) relieving the disease-state, e.g., causing regression of the disease state until a desired endpoint is reached. Treating also includes the amelioration of a symptom of a disease, wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to an indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Formulations and Dosages

The compounds of the present invention can be formulated as pharmaceutical compositions and administered to a human patient in a variety of forms adapted to the chosen route of administration, e.g., orally or parenterally, by intravenous (e.g., continuously or bolus), intrathecal, intramuscular, topical, intradermal, intraperitoneal, intraocular, inhalation or subcutaneous routes. Exemplary pharmaceutical compositions are disclosed in "*Remington: The Science and Practice of Pharmacy*," A. Gennaro, ed., 20th edition, Lippincott, Williams & Wilkins, Philadelphia, Pa.

Thus, the present compounds may be systemically administered, e.g., orally, in combination with a pharmaceutically acceptable carrier/excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level will be obtained.

The amount of the compound of the present invention or an active salt or derivative thereof, required for use in treatment will vary not only with the particular compound or salt selected but also with the route of administration, the nature of the condition being treated, and the age and condition of the patient, and will ultimately be at the discretion of the attendant physician or clinician. In general, however, a suitable dose will be in the range of (a) about 1.0-1000 mg/kg of body weight per day, (b) about 10-500 mg/kg of body weight per day, and (c) about 5-20 mg/kg of body weight per day.

For oral administration, the compounds of the present invention may be administered to an adult once or divided into several times at a dose of generally from 0.001 to 5000 mg per day, also from 0.1 to 2500 mg per day, and from 1 to 1000 mg per day.

For a liquid composition (e.g., in a lotion), the concentration of compounds of the present invention can be from (a) about 0.1-25 wt % and (b) about 0.5-10 wt %. The concentration in a semi-solid or solid composition such as a gel or a powder can be (a) about 0.1-5 wt % and (b) about 0.5-2.5 wt %.

The compounds of the present invention can be conveniently administered in unit dosage form; e.g., tablets, caplets, etc., containing (a) about 4-400 mg, (b) about 10-200 mg, and (c) about 20-100 mg of active ingredient per unit dosage form.

The compounds of the present invention can be administered to achieve peak plasma concentrations of the active compound of (a) about 0.02-20 µM, (b) about 0.1-10 µM, and (c) about 0.5-5 µM. These concentrations may be achieved, for example, by the intravenous injection (e.g., continuously or bolus) of a 0.005-0.5% solution of the active ingredient, oral administration as a bolus containing about 4-400 mg of the active ingredient, or by continuous intervenous infusion.

When a compound of the present invention is administered in combination with another agent or agents (e.g., co-administered), then the compound of the present invention and other agent can be administered simultaneously or in any order. They can be administered as a single pharmaceutical composition or as separate compositions. The administration of the compound of the present invention can be prior to the other agent(s), within minutes thereof, or up to hours (e.g., 24 or 48) or even days after the administration of the other agent(s). For example, the administration of the compound of the present invention can be within about 24 hours or within about 12 hours.

The tablets, troches, pills, capsules, sublingual tablets for rapid dissolution, or plastic strips impregnated with drug for buccal administration, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds of the present invention may also be administered intravenously (e.g., continuously or bolus) or intraperitoneally by infusion or injection. Solutions of the compounds of the present invention or their salts can be prepared in water, optionally mixed with a nontoxic surfactant. For solubility purposes the compound(s) may also be solubilized in a lipid emolusion or administered in liposomes. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions. Sterilization can also be performed by rapid heating and cooling.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

The desired dose of the compounds of the present invention may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Useful methods include, but are not limited to, those described below. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in th is field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

One stereoisomer of a compound of the present invention may be more potent than its counterpart(s). Thus, stereoisomers are included in the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Scheme 1 shows the preparation of sotalol analogs with sufonamido-nitrogen alkyl substituents with functionality to confer ultra-short activity to the molecules due to their propensity for rapid esterase hydrolysis to metabolites with greatly diminished or absence of parent compound activity. This approach has been duly demonstrated with esmolol and related compounds [J Med Chem 25, 1402 (1982); J Med Chem 25, 1408 (1982)]. An aminoacetophenone, in this case commercially available 4'-amino-2-bromo acetophenone in pyridine cooled to about −20° C. is treated with methyl (chlorosulfonyl)acetate to produce the sulfonamide (Step a). Subsequent treatment of the resulting acetophenone sulfonamide in acetonitrile, cooled to about 5° C., with excess isopropyl amine in acetonitrile will yield the amino ketone (Step b). Reduction of the ketone with sodium borohydride in alcohol solution affords the amino alcohol product (Step c). Alternatively, utilizing commercially available methyl 2-(chlorosulfonyl)propionate for the methyl (chlorosulfonyl)acetate will afford the amino alcohol product with an extended sulfonyl side-chain.

Scheme 2 shows the synthesis of various amino sidechains with ester functionality on the cyclic or alicyclic portion of the amino group. The commercially available 4'-amino acetophenone can be mesylated with methanesulfonyl chloride in pyridine at about −20° C. (step a). Conversion to the bromo ketone can be achieved by the addition of bromine to the 4-acetylmethanesulfonanilide in the presence of benzoyl chloride in an ether solvent (step b). Treatment of the bromo ketone with an excess of commercially available ethyl 3-aminobutyrate in acetonitrile can produce the amino ester (step c). Reduction of the ketone can be achieved with sodium borohydride in alcohol to afford the amino alcohol ester (step d). Reaction of an excess of an amino cyclohexyl carboxylic acid ester with the bromo ketone can result in cyclohexyl amino adduct (step e). Subsequent sodium borohydride treatment will produce the corresponding amino alcohol (step f). Condensation of the bromo ketone with 2-aminoisobutyric acid ester or 1-aminocyclopropane carboxylic acid ester should produce the corresponding amino ketones (step g) which upon sodium borohydride reduction can give the amino alcohols (step h).

Scheme 3

Scheme 3 shows the synthesis of a sotalol analog containing a carboxylic acid ester pendant on the aromatic ring. Commercially available 4-benzyloxy-3-nitro-acetophenone can be reduced to the aniline compound with Fe powder or SnCl$_2$ in ethanolic hydrochloric acid solution followed by basic work-up (step a). Treatment of the aniline with methane sulfonyl chloride in pyridine at about −20° C. to room temperature will produce the 4-benzyloxy-3-methanesulfonanmide acetophenone (step b). Conversion to the bromoketone can be achieved using bromine in the presence of benzoyl peroxide in a solvent such as diethyl ether (step c). Reaction of the bromoketone with an excess of isopropyl amine will afford the amino ketone (step d). Reduction of the ketone with sodium borohydride affords the amino alcohol, and removal of the benzyloxy group can be accomplished via treatment with hydrogen over a palladium/carbon catalyst (step e). Alkylation of the phenol can be accomplished with ethyl bromoacetate using basic media such as potassium carbonate in acetone under reflux to produce the ester (step f).

Other features of the invention will become apparent in the course of the following descriptions of exemplary embodiments that are given for illustration of the invention and are not intended to be limiting thereof.

EXAMPLES

The examples in the Tables below can be prepared according to the methods of the scheme numbers provided for each example.

TABLE 1

| Ex. # | R | m | Y | Synthesis Route |
|---|---|---|---|---|
| 1. | CH$_3$ | 0 | H | Scheme 1 |
| 2. | CH$_2$CH$_3$ | 0 | H | Scheme 1 |
| 3. | CH$_2$CH$_2$CH$_3$ | 0 | H | Scheme 1 |
| 4. | CH$_2$CH=CH$_2$ | 0 | H | Scheme 1 |
| 5. | CH$_3$ | 1 | H | Scheme 1 |
| 6. | CH$_2$CH$_3$ | 1 | H | Scheme 1 |
| 7. | CH$_2$CH$_2$CH$_3$ | 1 | H | Scheme 1 |
| 8. | CH$_2$CH=CH$_2$ | 1 | H | Scheme 1 |
| 9. | CH$_3$ | 2 | H | Scheme 1 |
| 10. | CH$_2$CH$_3$ | 2 | H | Scheme 1 |
| 11. | CH$_2$CH$_2$CH$_3$ | 2 | H | Scheme 1 |
| 12. | CH$_2$CH=CH$_2$ | 2 | H | Scheme 1 |
| 13. | CH$_3$ | 0 | CH$_3$ | Scheme 1 |
| 14. | CH$_2$CH$_3$ | 0 | CH$_3$ | Scheme 1 |
| 15. | CH$_2$CH$_2$CH$_3$ | 0 | CH$_3$ | Scheme 1 |
| 16. | CH$_2$CH=CH$_2$ | 0 | CH$_3$ | Scheme 1 |
| 17. | CH$_3$ | 1 | CH$_3$ | Scheme 1 |
| 18. | CH$_2$CH$_3$ | 1 | CH$_3$ | Scheme 1 |
| 19. | CH$_2$CH$_2$CH$_3$ | 1 | CH$_3$ | Scheme 1 |
| 20. | CH$_2$CH=CH$_2$ | 1 | CH$_3$ | Scheme 1 |
| 21. | CH$_3$ | 2 | CH$_3$ | Scheme 1 |
| 22. | CH$_2$CH$_3$ | 2 | CH$_3$ | Scheme 1 |
| 23. | CH$_2$CH$_2$CH$_3$ | 2 | CH$_3$ | Scheme 1 |
| 24. | CH$_2$CH=CH$_2$ | 2 | CH$_3$ | Scheme 1 |

TABLE 2

| Ex. # | R | m | Y | Synthesis Route |
|---|---|---|---|---|
| 1 | CH$_3$ | 0 | H | Scheme 2 |
| 2 | CH$_2$CH$_3$ | 0 | H | Scheme 2 |
| 3 | CH$_2$CH$_2$CH$_3$ | 0 | H | Scheme 2 |
| 4 | CH$_2$CH=CH$_2$ | 0 | H | Scheme 2 |
| 5 | CH$_3$ | 1 | H | Scheme 2 |
| 6 | CH$_2$CH$_3$ | 1 | H | Scheme 2 |
| 7 | CH$_2$CH$_2$CH$_3$ | 1 | H | Scheme 2 |
| 8 | CH$_2$CH=CH$_2$ | 1 | H | Scheme 2 |
| 9 | CH$_3$ | 2 | H | Scheme 2 |
| 10 | CH$_2$CH$_3$ | 2 | H | Scheme 2 |
| 11 | CH$_2$CH$_2$CH$_3$ | 2 | H | Scheme 2 |
| 12 | CH$_2$CH=CH$_2$ | 2 | H | Scheme 2 |
| 13 | CH$_3$ | 0 | CH$_3$ | Scheme 2 |
| 14 | CH$_2$CH$_3$ | 0 | CH$_3$ | Scheme 2 |
| 15 | CH$_2$CH$_2$CH$_3$ | 0 | CH$_3$ | Scheme 2 |
| 16 | CH$_2$CH=CH$_2$ | 0 | CH$_3$ | Scheme 2 |
| 17 | CH$_3$ | 1 | CH$_3$ | Scheme 2 |
| 18 | CH$_2$CH$_3$ | 1 | CH$_3$ | Scheme 2 |
| 19 | CH$_2$CH$_2$CH$_3$ | 1 | CH$_3$ | Scheme 2 |
| 20 | CH$_2$CH=CH$_2$ | 1 | CH$_3$ | Scheme 2 |
| 21 | CH$_3$ | 2 | CH$_3$ | Scheme 2 |
| 22 | CH$_2$CH$_3$ | 2 | CH$_3$ | Scheme 2 |
| 23 | CH$_2$CH$_2$CH$_3$ | 2 | CH$_3$ | Scheme 2 |
| 24 | CH$_2$CH=CH$_2$ | 2 | CH$_3$ | Scheme 2 |

TABLE 3

| Ex. # | R | m | Chain position | Synthesis Route |
|---|---|---|---|---|
| 1 | CH$_3$ | 0 | 1 | Scheme 2 |
| 2 | CH$_2$CH$_3$ | 0 | 1 | Scheme 2 |
| 3 | CH$_2$CH$_2$CH$_3$ | 0 | 1 | Scheme 2 |
| 4 | CH$_2$CH=CH$_2$ | 0 | 1 | Scheme 2 |
| 5 | CH$_3$ | 0 | 2 | Scheme 2 |
| 6 | CH$_2$CH$_3$ | 0 | 2 | Scheme 2 |
| 7 | CH$_2$CH$_2$CH$_3$ | 0 | 2 | Scheme 2 |
| 8 | CH$_2$CH=CH$_2$ | 0 | 2 | Scheme 2 |
| 9 | CH$_3$ | 1 | 1 | Scheme 2 |
| 10 | CH$_2$CH$_3$ | 1 | 1 | Scheme 2 |
| 11 | CH$_2$CH$_2$CH$_3$ | 1 | 1 | Scheme 2 |
| 12 | CH$_2$CH=CH$_2$ | 1 | 1 | Scheme 2 |
| 13 | CH$_3$ | 1 | 2 | Scheme 2 |
| 14 | CH$_2$CH$_3$ | 1 | 2 | Scheme 2 |
| 15 | CH$_2$CH$_2$CH$_3$ | 1 | 2 | Scheme 2 |
| 16 | CH$_2$CH=CH$_2$ | 1 | 2 | Scheme 2 |

TABLE 4

| Ex. # | R | m | Chain position | Synthesis Route |
|---|---|---|---|---|
| 1 | CH$_3$ | 0 | 1 | Scheme 2 |
| 2 | CH$_2$CH$_3$ | 0 | 1 | Scheme 2 |
| 3 | CH$_2$CH$_2$CH$_3$ | 0 | 1 | Scheme 2 |
| 4 | CH$_2$CH=CH$_2$ | 0 | 1 | Scheme 2 |
| 5 | CH$_3$ | 0 | 2 | Scheme 2 |
| 6 | CH$_2$CH$_3$ | 0 | 2 | Scheme 2 |
| 7 | CH$_2$CH$_2$CH$_3$ | 0 | 2 | Scheme 2 |
| 8 | CH$_2$CH=CH$_2$ | 0 | 2 | Scheme 2 |
| 9 | CH$_3$ | 1 | 1 | Scheme 2 |
| 10 | CH$_2$CH$_3$ | 1 | 1 | Scheme 2 |
| 11 | CH$_2$CH$_2$CH$_3$ | 1 | 1 | Scheme 2 |
| 12 | CH$_2$CH=CH$_2$ | 1 | 1 | Scheme 2 |
| 13 | CH$_3$ | 1 | 2 | Scheme 2 |
| 14 | CH$_2$CH$_3$ | 1 | 2 | Scheme 2 |
| 15 | CH$_2$CH$_2$CH$_3$ | 1 | 2 | Scheme 2 |
| 16 | CH$_2$CH=CH$_2$ | 1 | 2 | Scheme 2 |

TABLE 5

| Ex. # | R | m | Chain position | Synthesis Route |
|---|---|---|---|---|
| 1 | CH$_3$ | 0 | 1 | Scheme 2 |
| 2 | CH$_2$CH$_3$ | 0 | 1 | Scheme 2 |
| 3 | CH$_2$CH$_2$CH$_3$ | 0 | 1 | Scheme 2 |
| 4 | CH$_2$CH=CH$_2$ | 0 | 1 | Scheme 2 |
| 5 | CH$_3$ | 0 | 2 | Scheme 2 |
| 6 | CH$_2$CH$_3$ | 0 | 2 | Scheme 2 |
| 7 | CH$_2$CH$_2$CH$_3$ | 0 | 2 | Scheme 2 |
| 8 | CH$_2$CH=CH$_2$ | 0 | 2 | Scheme 2 |
| 9 | CH$_3$ | 0 | 3 | Scheme 2 |
| 10 | CH$_2$CH$_3$ | 0 | 3 | Scheme 2 |
| 11 | CH$_2$CH$_2$CH$_3$ | 0 | 3 | Scheme 2 |
| 12 | CH$_2$CH=CH$_2$ | 0 | 3 | Scheme 2 |
| 13 | CH$_3$ | 1 | 1 | Scheme 2 |
| 14 | CH$_2$CH$_3$ | 1 | 1 | Scheme 2 |
| 15 | CH$_2$CH$_2$CH$_3$ | 1 | 1 | Scheme 2 |
| 16 | CH$_2$CH=CH$_2$ | 1 | 1 | Scheme 2 |
| 17 | CH$_3$ | 1 | 2 | Scheme 2 |
| 18 | CH$_2$CH$_3$ | 1 | 2 | Scheme 2 |
| 19 | CH$_2$CH$_2$CH$_3$ | 1 | 2 | Scheme 2 |
| 20 | CH$_2$CH=CH$_2$ | 1 | 2 | Scheme 2 |
| 21 | CH$_3$ | 0 | 3 | Scheme 2 |
| 22 | CH$_2$CH$_3$ | 0 | 3 | Scheme 2 |
| 23 | CH$_2$CH$_2$CH$_3$ | 0 | 3 | Scheme 2 |
| 24 | CH$_2$CH=CH$_2$ | 0 | 3 | Scheme 2 |

TABLE 6

| Ex. # | R | m | Synthesis Route |
|---|---|---|---|
| 1 | CH$_3$ | 0 | Scheme 2 |
| 2 | CH$_2$CH$_3$ | 0 | Scheme 2 |
| 3 | CH$_2$CH$_2$CH$_3$ | 0 | Scheme 2 |
| 4 | CH$_2$CH=CH$_2$ | 0 | Scheme 2 |
| 5 | CH$_3$ | 1 | Scheme 2 |
| 6 | CH$_2$CH$_3$ | 1 | Scheme 2 |
| 7 | CH$_2$CH$_2$CH$_3$ | 1 | Scheme 2 |
| 8 | CH$_2$CH=CH$_2$ | 1 | Scheme 2 |

TABLE 7

| Ex. # | R | m | Chain position | Synthesis Route |
|---|---|---|---|---|
| 1 | CH$_3$ | 0 | 1 | Scheme 2 |
| 2 | CH$_2$CH$_3$ | 0 | 1 | Scheme 2 |
| 3 | CH$_2$CH$_2$CH$_3$ | 0 | 1 | Scheme 2 |
| 4 | CH$_2$CH=CH$_2$ | 0 | 1 | Scheme 2 |
| 5 | CH$_3$ | 1 | 1 | Scheme 2 |
| 6 | CH$_2$CH$_3$ | 1 | 1 | Scheme 2 |
| 7 | CH$_2$CH$_2$CH$_3$ | 1 | 1 | Scheme 2 |
| 8 | CH$_2$CH=CH$_2$ | 1 | 1 | Scheme 2 |
| 9 | CH$_3$ | 0 | 2 | Scheme 2 |
| 10 | CH$_2$CH$_3$ | 0 | 2 | Scheme 2 |
| 11 | CH$_2$CH$_2$CH$_3$ | 0 | 2 | Scheme 2 |
| 12 | CH$_2$CH=CH$_2$ | 0 | 2 | Scheme 2 |
| 13 | CH$_3$ | 1 | 2 | Scheme 2 |
| 14 | CH$_2$CH$_3$ | 1 | 2 | Scheme 2 |
| 15 | CH$_2$CH$_2$CH$_3$ | 1 | 2 | Scheme 2 |
| 16 | CH$_2$CH=CH$_2$ | 1 | 2 | Scheme 2 |

TABLE 8

| Ex. # | R | n | N-Chain position | O-Chain position | Synthesis Route |
|---|---|---|---|---|---|
| 1 | CH$_3$ | 1 | 3 | 4 | Scheme 3 |
| 2 | CH$_2$CH$_3$ | 1 | 3 | 4 | Scheme 3 |
| 3 | CH$_2$CH$_2$CH$_3$ | 1 | 3 | 4 | Scheme 3 |
| 4 | CH$_2$CH=CH$_2$ | 1 | 3 | 4 | Scheme 3 |
| 5 | CH$_3$ | 1 | 4 | 3 | Scheme 3 |
| 6 | CH$_2$CH$_3$ | 1 | 4 | 3 | Scheme 3 |
| 7 | CH$_2$CH$_2$CH$_3$ | 1 | 4 | 3 | Scheme 3 |
| 8 | CH$_2$CH=CH$_2$ | 1 | 4 | 3 | Scheme 3 |
| 1 | CH$_3$ | 2 | 3 | 4 | Scheme 3 |

TABLE 8-continued

| Ex. # | R | n | N-Chain position | O-Chain position | Synthesis Route |
|---|---|---|---|---|---|
| 2 | $CH_2CH_3$ | 2 | 3 | 4 | Scheme 3 |
| 3 | $CH_2CH_2CH_3$ | 2 | 3 | 4 | Scheme 3 |
| 4 | $CH_2CH=CH_2$ | 2 | 3 | 4 | Scheme 3 |
| 5 | $CH_3$ | 2 | 4 | 3 | Scheme 3 |
| 6 | $CH_2CH_3$ | 2 | 4 | 3 | Scheme 3 |
| 7 | $CH_2CH_2CH_3$ | 2 | 4 | 3 | Scheme 3 |
| 8 | $CH_2CH=CH_2$ | 2 | 4 | 3 | Scheme 3 |

Example 1

Table 1, Example 1 (above left) and its corresponding acid (above right) were synthesized according to Scheme 1. These compounds were then tested as follows.

A set of whole-cell, voltage-clamp experiments was performed using a HEKA® EPC 9 amplifier. Data was recorded and analyzed using the HEKA® Patchmaster and Fitmaster software. At the time of the recordings, cell culture media was replaced by a bath solution (containing (mM): 137 NaCl, 4 KCl, 1.8 CaCl2, 10 HEPES, and 10 glucose, pH adjusted to 7.4 with NaOH). The pipette solution containing different concentrations of the drug to test was introduced. Borosilicate glass electrodes (tip resistant 2-5 MΩ) were filled with internal solution (containing (mM): 130 KCl, 1 MgCl2, 5 EGTA, 5 MgATP and 10 HEPES, pH adjusted to 7.2 with KOH). Tail currents were measured at repolarizing test potentials (−100 to +40 mV, 4 seconds each) following a one second depolarizing step to +60 mV from a holding potential of −80 mV. Cell recordings were performed in a minimum of 2 plates (3-5 cells/plate) for each EFV concentration and compared to control.

In hERG-HEK cells that were transiently transferred with CYP2B6*1 cDNA, tail current recordings were performed using the following 2-sweep voltage clamp protocol: membrane potential was held at −80 mV, increased to 60 mV (1 second), and currents were measured during two repolarizing steps at −100 and −20 mV (5 seconds each). This protocol was performed twice for each cell at 1 and 2 minutes following cytosolic access and exposure to the pipette solution to evaluate the influence of incubation time on drug mediated alterations in hERG channel conductivity. A sigmoidal Emax model was fit to the EFV inhibitory effect on 1hERG using Prism (GraphPad Software, Inc., La Jolla, Calif.).

Sotalol ester, soestolol (ester A, Table 1, Example 1) and its corresponding acid (ester C) were evaluated. The studies were performed blinded with the operator unaware of the chemical structure of Ester A or Ester C. Additionally, the vehicle the esters are dissolved in was studied, as well as sotalol and dofetilide. Dofetilide is a very potent Class III anti-arrhythmic with known potent inhibition of the K+ channel IKr. The drug is available in the U.S. to treat arrhythmias and is used in these experiments as a standard to compare the effect of other drugs to that of dofetilide, the most potent K channel inhibitor, effective in microgram quantities (see FIGS. 1 & 2).

Figure 1:
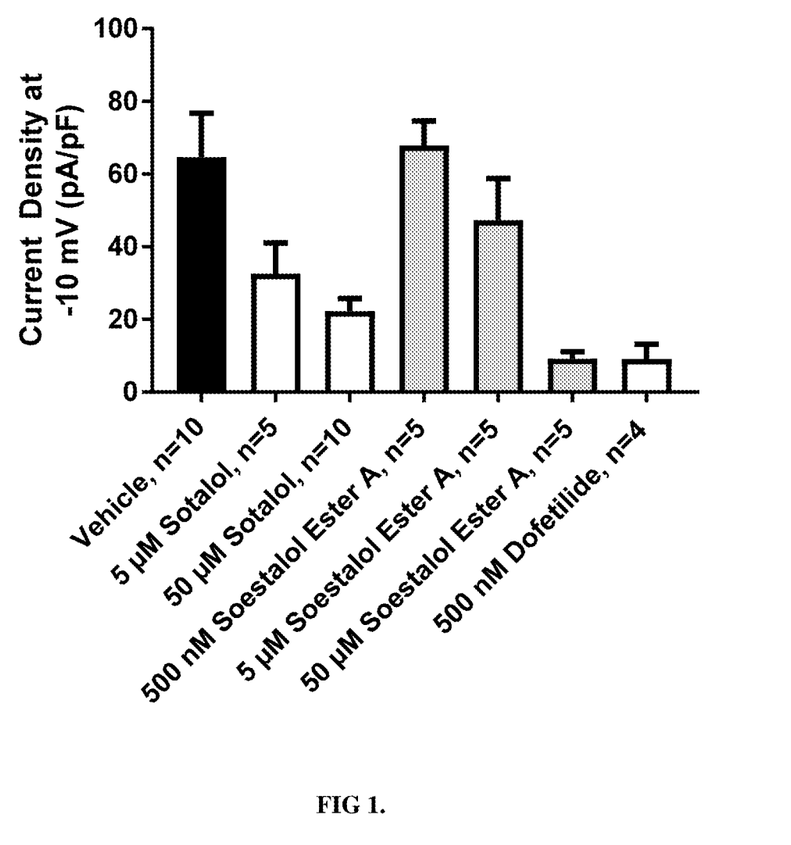
FIG. 1 shows the results of current density experiments with Sotalol Ester A.
Figure 2:
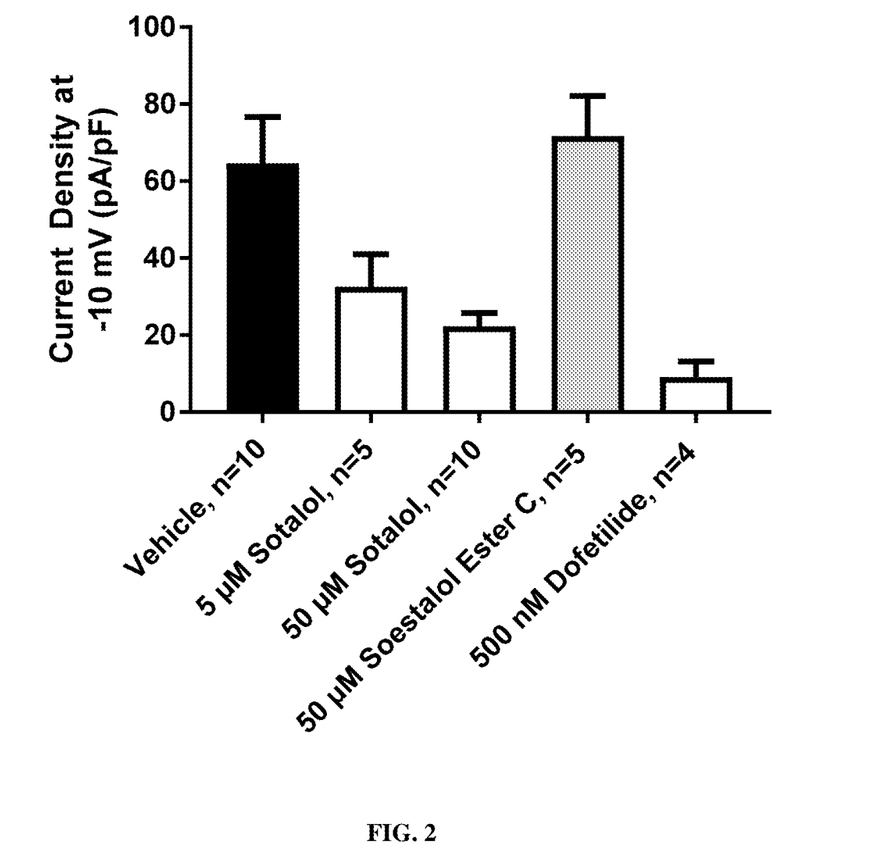
FIG. 2 shows the results of current density experiments with Sotalol Ester C.

The effects of ester A, vehicle, ester C, and dofetilide were evaluated on current density in FIGS. 1 & 2. FIG. 1 shows that the control current is unaffected by vehicle. Sotalol caused a dose related inhibition of K flux, as shown by the reduction in current at 5 μm sotalol and then a further reduction by 10 μm sotalol. A very low dose (500 nM) of the sotalol ester (soestolol-ester A) showed no inhibition in current. Ester A at 5 μm and 50 μm showed a dose dependent reduction in current. This confirms that the ester is an active inhibitor of the potassium channel. The 50 μm dose of soestolol is significantly more potent than the corresponding sotalol dose. It is as potent as the 500 nM concentration of dofetilide on K current (FIG. 1).

The data shown in FIG. 2 supports our thesis that an ester introduced into the sotalol molecule may beneficially shorten its activity. We see in FIG. 2 that ester C, which is the acid functionary, of Ester A has no activity—showing the same current effect to that seen with vehicle. That the assay is sensitive is demonstrated by a dose related reduction in current seen with sotalol 5 μM & 50 μM, as well as a marked current inhibition by dofetilide 500 nM concentration.

One skilled in the art can see from FIGS. 1 & 2 that an ester of sotalol is an active inhibitor of the potassium channel with similar activity to known clinically useful Class III anti-arrhythmic agents (sotalol and dofetilide). When the ester is hydrolyzed to an acid it is no longer active on the potassium channel. This loss of activity on the K channel would correlate with a loss of biologic activity as an anti-arrhythmic drug. Thus, the bodies esterase's are predicted to metabolize the ester (active class III agent) to the inactive acid. This cascade would predict a short half-life for the ester A-soestolol, and thus its favorable kinetics in man.

Numerous modifications and variations of the present invention are possible in light of the above teachings. It is therefore to be understood that within the scope of the appended claims, the invention may be practiced otherwise than as specifically described herein.

What is claimed is:

1. A pharmaceutical composition, comprising: a therapeutically effective amount of a compound of one of Formulae 1-5 or a stereoisomer or a pharmaceutically acceptable salt thereof and a pharmaceutically acceptable carrier:

Formula 1

Formula 2

Formula 3

Formula 4

Formula 5 wherein:

R is selected from H, $C_{1-6}$ alkyl, $C_{3-6}$ alkenyl, and $C_{3-6}$ alkynyl;

m is selected from 0, 1, and 2;

n is selected from 0, 1, 2, and 3;

X, $X^1$, $X^2$, and $X^3$ are H;

Y is selected from H and $C_{1-3}$ alkyl; and,

Z is $CH_3$.

2. The pharmaceutical composition of claim 1, wherein the compound is selected from the table below:

| Ex. # | R | m | Y |
|---|---|---|---|
| 1. | $CH_3$ | 0 | H |
| 2. | $CH_2CH_3$ | 0 | H |
| 3. | $CH_2CH_2CH_3$ | 0 | H |
| 4. | $CH_2CH=CH_2$ | 0 | H |
| 5. | $CH_3$ | 1 | H |
| 6. | $CH_2CH_3$ | 1 | H |
| 7. | $CH_2CH_2CH_3$ | 1 | H |
| 8. | $CH_2CH=CH_2$ | 1 | H |
| 9. | $CH_3$ | 2 | H |
| 10. | $CH_2CH_3$ | 2 | H |
| 11. | $CH_2CH_2CH_3$ | 2 | H |
| 12. | $CH_2CH=CH_2$ | 2 | H |
| 13. | $CH_3$ | 0 | $CH_3$ |
| 14. | $CH_2CH_3$ | 0 | $CH_3$ |
| 15. | $CH_2CH_2CH_3$ | 0 | $CH_3$ |
| 16. | $CH_2CH=CH_2$ | 0 | $CH_3$ |
| 17. | $CH_3$ | 1 | $CH_3$ |
| 18. | $CH_2CH_3$ | 1 | $CH_3$ |
| 19. | $CH_2CH_2CH_3$ | 1 | $CH_3$ |
| 20. | $CH_2CH=CH_2$ | 1 | $CH_3$ |
| 21. | $CH_3$ | 2 | $CH_3$ |
| 22. | $CH_2CH_3$ | 2 | $CH_3$ |
| 23. | $CH_2CH_2CH_3$ | 2 | $CH_3$ |
| 24. | $CH_2CH=CH_2$ | 2 | $CH_3$ | or a stereoisomer or a pharmaceutically acceptable salt thereof.

3. The pharmaceutical composition of claim 1, wherein the compound is selected from the table below:

| Ex. # | R | m | Y |
|---|---|---|---|
| 1 | $CH_3$ | 0 | H |
| 2 | $CH_2CH_3$ | 0 | H |
| 3 | $CH_2CH_2CH_3$ | 0 | H |
| 4 | $CH_2CH=CH_2$ | 0 | H |
| 5 | $CH_3$ | 1 | H |
| 6 | $CH_2CH_3$ | 1 | H |
| 7 | $CH_2CH_2CH_3$ | 1 | H |
| 8 | $CH_2CH=CH_2$ | 1 | H |
| 9 | $CH_3$ | 2 | H |
| 10 | $CH_2CH_3$ | 2 | H |
| 11 | $CH_2CH_2CH_3$ | 2 | H |
| 12 | $CH_2CH=CH_2$ | 2 | H |
| 13 | $CH_3$ | 0 | $CH_3$ |
| 14 | $CH_2CH_3$ | 0 | $CH_3$ |
| 15 | $CH_2CH_2CH_3$ | 0 | $CH_3$ |
| 16 | $CH_2CH=CH_2$ | 0 | $CH_3$ |
| 17 | $CH_3$ | 1 | $CH_3$ |
| 18 | $CH_2CH_3$ | 1 | $CH_3$ |
| 19 | $CH_2CH_2CH_3$ | 1 | $CH_3$ |
| 20 | $CH_2CH=CH_2$ | 1 | $CH_3$ |
| 21 | $CH_3$ | 2 | $CH_3$ |
| 22 | $CH_2CH_3$ | 2 | $CH_3$ |
| 23 | $CH_2CH_2CH_3$ | 2 | $CH_3$ |
| 24 | $CH_2CH=CH_2$ | 2 | $CH_3$ | or a stereoisomer or a pharmaceutically acceptable salt thereof.

4. The pharmaceutical composition of claim 1, wherein the compound is selected from the table below:

| Ex. # | R | m | Chain position |
|---|---|---|---|
| 1 | $CH_3$ | 0 | 1 |
| 2 | $CH_2CH_3$ | 0 | 1 |
| 3 | $CH_2CH_2CH_3$ | 0 | 1 |
| 4 | $CH_2CH=CH_2$ | 0 | 1 |
| 5 | $CH_3$ | 0 | 2 |
| 6 | $CH_2CH_3$ | 0 | 2 |
| 7 | $CH_2CH_2CH_3$ | 0 | 2 |
| 8 | $CH_2CH=CH_2$ | 0 | 2 |
| 9 | $CH_3$ | 1 | 1 |
| 10 | $CH_2CH_3$ | 1 | 1 |
| 11 | $CH_2CH_2CH_3$ | 1 | 1 |
| 12 | $CH_2CH=CH_2$ | 1 | 1 |
| 13 | $CH_3$ | 1 | 2 |
| 14 | $CH_2CH_3$ | 1 | 2 |
| 15 | $CH_2CH_2CH_3$ | 1 | 2 |
| 16 | $CH_2CH=CH_2$ | 1 | 2 | or a stereoisomer or a pharmaceutically acceptable salt thereof.

5. The pharmaceutical composition of claim 1, wherein the compound is selected from the table below:

| Ex. # | R | m | Chain position |
|---|---|---|---|
| 1 | $CH_3$ | 0 | 1 |
| 2 | $CH_2CH_3$ | 0 | 1 |
| 3 | $CH_2CH_2CH_3$ | 0 | 1 |
| 4 | $CH_2CH=CH_2$ | 0 | 1 |
| 5 | $CH_3$ | 0 | 2 |
| 6 | $CH_2CH_3$ | 0 | 2 |
| 7 | $CH_2CH_2CH_3$ | 0 | 2 |
| 8 | $CH_2CH=CH_2$ | 0 | 2 |
| 9 | $CH_3$ | 1 | 1 |
| 10 | $CH_2CH_3$ | 1 | 1 |
| 11 | $CH_2CH_2CH_3$ | 1 | 1 |
| 12 | $CH_2CH=CH_2$ | 1 | 1 |
| 13 | $CH_3$ | 1 | 2 |
| 14 | $CH_2CH_3$ | 1 | 2 |
| 15 | $CH_2CH_2CH_3$ | 1 | 2 |
| 16 | $CH_2CH=CH_2$ | 1 | 2 | or a stereoisomer or a pharmaceutically acceptable salt thereof.

6. The pharmaceutical composition of claim 1, wherein the compound is selected from the table below:

| Ex. # | R | m | Chain position |
|---|---|---|---|
| 1 | $CH_3$ | 0 | 1 |
| 2 | $CH_2CH_3$ | 0 | 1 |
| 3 | $CH_2CH_2CH_3$ | 0 | 1 |
| 4 | $CH_2CH=CH_2$ | 0 | 1 |
| 5 | $CH_3$ | 0 | 2 |
| 6 | $CH_2CH_3$ | 0 | 2 |
| 7 | $CH_2CH_2CH_3$ | 0 | 2 |
| 8 | $CH_2CH=CH_2$ | 0 | 2 |
| 9 | $CH_3$ | 0 | 3 |
| 10 | $CH_2CH_3$ | 0 | 3 |
| 11 | $CH_2CH_2CH_3$ | 0 | 3 |
| 12 | $CH_2CH=CH_2$ | 0 | 3 |
| 13 | $CH_3$ | 1 | 1 |
| 14 | $CH_2CH_3$ | 1 | 1 |
| 15 | $CH_2CH_2CH_3$ | 1 | 1 |
| 16 | $CH_2CH=CH_2$ | 1 | 1 |
| 17 | $CH_3$ | 1 | 2 |
| 18 | $CH_2CH_3$ | 1 | 2 |
| 19 | $CH_2CH_2CH_3$ | 1 | 2 |
| 20 | $CH_2CH=CH_2$ | 1 | 2 |
| 21 | $CH_3$ | 0 | 3 |
| 22 | $CH_2CH_3$ | 0 | 3 |
| 23 | $CH_2CH_2CH_3$ | 0 | 3 |
| 24 | $CH_2CH=CH_2$ | 0 | 3 | or a stereoisomer or a pharmaceutically acceptable salt thereof.

7. The pharmaceutical composition of claim 1, wherein the compound is selected from the table below:

| Ex. # | R | m |
|---|---|---|
| 1 | $CH_3$ | 0 |
| 2 | $CH_2CH_3$ | 0 |
| 3 | $CH_2CH_2CH_3$ | 0 |
| 4 | $CH_2CH=CH_2$ | 0 |
| 5 | $CH_3$ | 1 |
| 6 | $CH_2CH_3$ | 1 |
| 7 | $CH_2CH_2CH_3$ | 1 |
| 8 | $CH_2CH=CH_2$ | 1 | or a stereoisomer or a pharmaceutically acceptable salt thereof.

8. The pharmaceutical composition of claim 1, wherein the compound is selected from the table below:

| Ex. # | R | m | Chain position |
|---|---|---|---|
| 1 | CH$_3$ | 0 | 1 |
| 2 | CH$_2$CH$_3$ | 0 | 1 |
| 3 | CH$_2$CH$_2$CH$_3$ | 0 | 1 |
| 4 | CH$_2$CH=CH$_2$ | 0 | 1 |
| 5 | CH$_3$ | 1 | 1 |
| 6 | CH$_2$CH$_3$ | 1 | 1 |
| 7 | CH$_2$CH$_2$CH$_3$ | 1 | 1 |
| 8 | CH$_2$CH=CH$_2$ | 1 | 1 |
| 9 | CH$_3$ | 0 | 2 |
| 10 | CH$_2$CH$_3$ | 0 | 2 |
| 11 | CH$_2$CH$_2$CH$_3$ | 0 | 2 |
| 12 | CH$_2$CH=CH$_2$ | 0 | 2 |
| 13 | CH$_3$ | 1 | 2 |
| 14 | CH$_2$CH$_3$ | 1 | 2 |
| 15 | CH$_2$CH$_2$CH$_3$ | 1 | 2 |
| 16 | CH$_2$CH=CH$_2$ | 1 | 2 | or a stereoisomer or a pharmaceutically acceptable salt thereof.

9. The pharmaceutical composition of claim 1, wherein the compound is selected from the table below:

| Ex. # | R | n | N-Chain position | O-Chain position |
|---|---|---|---|---|
| 1 | CH$_3$ | 1 | 3 | 4 |
| 2 | CH$_2$CH$_3$ | 1 | 3 | 4 |
| 3 | CH$_2$CH$_2$CH$_3$ | 1 | 3 | 4 |
| 4 | CH$_2$CH=CH$_2$ | 1 | 3 | 4 |
| 5 | CH$_3$ | 1 | 4 | 3 |
| 6 | CH$_2$CH$_3$ | 1 | 4 | 3 |
| 7 | CH$_2$CH$_2$CH$_3$ | 1 | 4 | 3 |
| 8 | CH$_2$CH=CH$_2$ | 1 | 4 | 3 |
| 9 | CH$_3$ | 2 | 3 | 4 |
| 10 | CH$_2$CH$_3$ | 2 | 3 | 4 |
| 11 | CH$_2$CH$_2$CH$_3$ | 2 | 3 | 4 |
| 12 | CH$_2$CH=CH$_2$ | 2 | 3 | 4 |
| 13 | CH$_3$ | 2 | 4 | 3 |
| 14 | CH$_2$CH$_3$ | 2 | 4 | 3 |
| 15 | CH$_2$CH$_2$CH$_3$ | 2 | 4 | 3 |
| 16 | CH$_2$CH=CH$_2$ | 2 | 4 | 3 | or a stereoisomer or a pharmaceutically acceptable salt thereof.

10. A method of terminating or blocking the occurrence of an arrhythmia, comprising: administering to a patient in need thereof a therapeutically effective amount of the pharmaceutical composition of claim 1, wherein the arrhythmia is selected from: paroxysmal atrial tachycardia, junctional ectopic tachycardia, atrial flutter, atrial fibrillation, atrial tachycardia, ventricular tachycardia, junctional tachycardia, and ventricular fibrillation.

11. A method of causing electrophysiological actions that are anti-arrhythmic, comprising: administering to a patient in need thereof a therapeutically effective amount of the pharmaceutical composition of claim 1, wherein the compound binds to the IKr and possibly IKs potassium channels, inhibiting them.

12. A method of terminating a symptom selected from: paroxysmal atrial tachycardia, junctional ectopic tachycardia, atrial flutter, atrial fibrillation, atrial tachycardia, junctional tachycardia, ventricular tachycardia, and ventricular fibrillation, comprising: administering to a patient in need thereof a therapeutically effective amount of the pharmaceutical composition of claim 1.

13. A method of blocking the development of or blocking a symptom selected from: paroxysmal atrial tachycardia, junctional ectopic tachycardia, atrial flutter, atrial fibrillation, atrial tachycardia, junctional tachycardia, ventricular tachycardia, and ventricular fibrillation, comprising: administering to a patient in need thereof a therapeutically effective amount of the pharmaceutical composition of claim 1.

14. The method of claim 13, wherein the patient had previously suffered from at least one of the symptoms and the therapy stops the reoccurrence of the symptom.

15. A method of treating a symptom selected from: paroxysmal atrial tachycardia junctional ectopic tachycardia, atrial flutter, and atrial fibrillation that occurs peri or post-operatively in the pediatric or adult population, comprising:

administering to a patient in need thereof the pharmaceutical composition of claim 1.

16. The method of claim 15, wherein the route of administration is selected from: intravenous, oral, topical, sublingual, and buccal.

* * * * *